(12) United States Patent
Chen

(10) Patent No.: US 8,587,447 B2
(45) Date of Patent: Nov. 19, 2013

(54) EARLY WARNING METHOD AND DEVICE FOR ULTRASONIC PROBE AND ULTRASONIC APPARATUS

(75) Inventor: You Chen, Wuxi (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 381 days.

(21) Appl. No.: 12/979,887

(22) Filed: Dec. 28, 2010

(65) Prior Publication Data

US 2011/0156922 A1    Jun. 30, 2011

(30) Foreign Application Priority Data

Dec. 28, 2009    (CN) .......................... 2009 1 0265635

(51) Int. Cl.
*G07C 3/00*    (2006.01)
(52) U.S. Cl.
USPC ............................ 340/679; 340/517; 340/665
(58) Field of Classification Search
None
See application file for complete search history.

(56) References Cited

U.S. PATENT DOCUMENTS

| | | | |
|---|---|---|---|
| 5,487,386 A * | 1/1996 | Wakabayashi et al. ....... 600/437 |
| 5,950,147 A | 9/1999 | Sarangapani et al. |
| 6,119,074 A | 9/2000 | Sarangapani |
| 6,336,065 B1 | 1/2002 | Gibson et al. |
| 6,338,152 B1 | 1/2002 | Fera et al. |
| 6,442,511 B1 | 8/2002 | Sarangapani et al. |
| 6,656,119 B2 * | 12/2003 | Sasaki et al. .................. 600/437 |
| 6,865,512 B2 * | 3/2005 | Hendrickson ................. 702/183 |
| 2004/0122618 A1 * | 6/2004 | Suzuki et al. ................. 702/181 |
| 2005/0228617 A1 * | 10/2005 | Kerwin et al. ............... 702/187 |
| 2008/0028860 A1 | 2/2008 | Refko et al. |
| 2009/0312999 A1 | 12/2009 | Kasztenny et al. |
| 2010/0042368 A1 * | 2/2010 | Lovelace et al. .............. 702/184 |

* cited by examiner

*Primary Examiner* — Mohammad Ghayour
*Assistant Examiner* — Brian Wilson
(74) *Attorney, Agent, or Firm* — Armstrong Teasdale LLP

(57) ABSTRACT

An early warning device for use with an ultrasonic probe includes a service lifetime acquisition unit configured to acquire service lifetimes of individual parts of the ultrasonic probe, a total working time acquisition unit configured to acquire total working times of the individual parts of the ultrasonic probe, a calculation unit configured to calculate existing service lifetime percents depending on the service lifetimes and the total working times, and a judgment and warning unit configured to determine whether any of the existing service lifetime percents is less than a threshold value, and to issue a warning if the existing service lifetime is less than the threshold value.

18 Claims, 4 Drawing Sheets

EARLY WARNING METHOD AND DEVICE FOR ULTRASONIC PROBE AND ULTRASONIC APPARATUS

CROSS REFERENCE TO RELATED APPLICATIONS

This application claims the benefit of Chinese Patent Application No. 200910265635.3 filed Dec. 28, 2009, which is hereby incorporated by reference in its entirety.

BACKGROUND OF THE INVENTION

The present invention generally relates to the ultrasonic field, particularly relates to an early warning method and device for an ultrasonic probe and an ultrasonic apparatus.

At present, ultrasonic techniques are more and more applied to the medical field: an image is formed by approaching an ultrasonic probe to an object to be imaged to assist a doctor with diagnose, wherein a real-time volume probe can provide a real-time three-dimensional ultrasonic image for the doctor.

Some parts of this real-time volume ultrasonic probe, such as motors, gear boxes, belt systems, etc., are easily worn out. These parts have limited service lifetimes. For example, the service lifetime of the gear box is about million cycles. It is impossible to predict existing service lifetimes during which these easy wear-out parts can work properly, so a user always suddenly encounters that the ultrasonic probe cannot work properly. At this time, the probe has to be stopped for a service person's check and maintenance. However, the service person cannot come here in time usually, so precious working time loses.

Meanwhile, the ultrasonic probe is not always put into the normal using condition. Over thermal, over current, over voltage and other extreme conditions may occur during application of the ultrasonic. When the ultrasonic probe is down, a service person can only relay on his/her experience to analyze what causes the probe to break down, and even sometimes the service person needs to "open" (destroy) the probe to look into the detail. If the service person can obtain some information related to the real-time working environment and field prior to failure of the probe, it will help the service person much to find the root cause of problems quickly.

BRIEF DESCRIPTION OF THE INVENTION

The main technical problem to be solved by the present invention is to provide an early warning method and device for an ultrasonic probe and an ultrasonic apparatus.

In order to solve the aforesaid problem, the technical solution of the ultrasonic probe early warning method of the invention includes acquiring service lifetimes of individual parts of the ultrasonic probe, acquiring total working times of the individual parts, acquiring existing service lifetime percents depending on the service lifetimes and the total working times, and issuing a warning if any of the existing service lifetime percents is less than a threshold value.

In some embodiments, the service lifetimes are present in a configuration file.

In some embodiments, acquiring total working times of the individual parts includes, for a gearbox, using the following equation:

a total working time of a gearbox=probe swing angle× link rod swing ratio×times of probe swing; and for a motor, using the following equation:

a total working time of a motor=working cycles of a gearbox×reduction ratio of a gearbox.

Further, the early warning method for an ultrasonic probe according to the present invention comprises storing the obtained total working times in a nonvolatile memory within the ultrasonic probe.

Wherein, for the step of acquiring existing service lifetime percents depending on the service lifetimes and the total working times, calculation is performed with the following equation:

existing service lifetime percents=((service lifetimes– total working times)/service lifetimes)×100%.

Further, the early warning method for an ultrasonic probe according to the present invention comprises acquiring parameters of the environment where the ultrasonic probe is and storing the environment parameters in the nonvolatile memory.

The environment parameters include a real-time voltage, a real-time electric current and temperature.

The warning is delivered to a maintenance station by email.

The warning is ejected in the form of a dialogue box and is displayed on a display interface.

Accordingly, an early warning device for an ultrasonic probe includes a service lifetime acquisition unit for acquiring service lifetimes of individual parts of the ultrasonic probe, a total working time acquisition unit for acquiring total working times of the individual parts of the ultrasonic probe, a calculation unit for calculating existing service lifetime percents depending on the service lifetimes and the total working times, and a judgment and warning unit for judging if any of the existing service lifetime percents is less than a threshold value, and issuing a warning if the existing service lifetime is less than the threshold value.

The service lifetimes are present in a configuration file.

The unit for acquiring the total working times includes a total working time acquisition unit of a gearbox, configured to calculate the total working time of the gearbox using the following equation:

probe swing angle×link rod swing ratio×times of probe swing; and a total working time acquisition unit of a motor, configured to calculate the total working time of the motor using the following equation:

working cycles of a gearbox×reduction ratio of a gearbox.

Further, the early warning device for an ultrasonic probe according to the present invention comprises a nonvolatile memory within the ultrasonic probe for storing the obtained total working times of the individual parts.

The calculation unit performs calculation by the following equation:

existing service lifetime percents=((service lifetimes– total working times)/service lifetimes)×100%.

Further, the early warning device for an ultrasonic probe according to the present invention comprises a unit for acquiring environment parameters, configured to acquire parameters of the environment where the ultrasonic probe is.

The environmental parameters are stored in the nonvolatile memory.

The environment parameters include a real-time voltage, a real-time electric current and temperature.

The warning is delivered to a maintenance station by email.

In addition, the present invention also discloses an ultrasonic apparatus, which comprises the early warning device for an ultrasonic probe.

The present invention acquires the service lifetimes and the total working times of individual parts of the ultrasonic probe and then acquires the existing service lifetime percent; besides, it is determined whether any of the existing service lifetime percents is less than the threshold value; the warning is issued if the existing service lifetime is less than the threshold value. Therefore, the ultrasonic probe can be effectively handled just prior to the failure but not subsequent to the failure; as a result, it is avoidable that the user will not suffer from the inconvenience caused by the failure of the ultrasonic probe.

BRIEF DESCRIPTION OF THE DRAWINGS

In order to thoroughly understanding the disclosure, reference is made to the following descriptions in conjunction with figures, in which.

DETAILED DESCRIPTION OF THE INVENTION

The embodiments of the present invention are described in detail as follows, but the present invention is not limited to the following specific embodiments.

Figure 1:
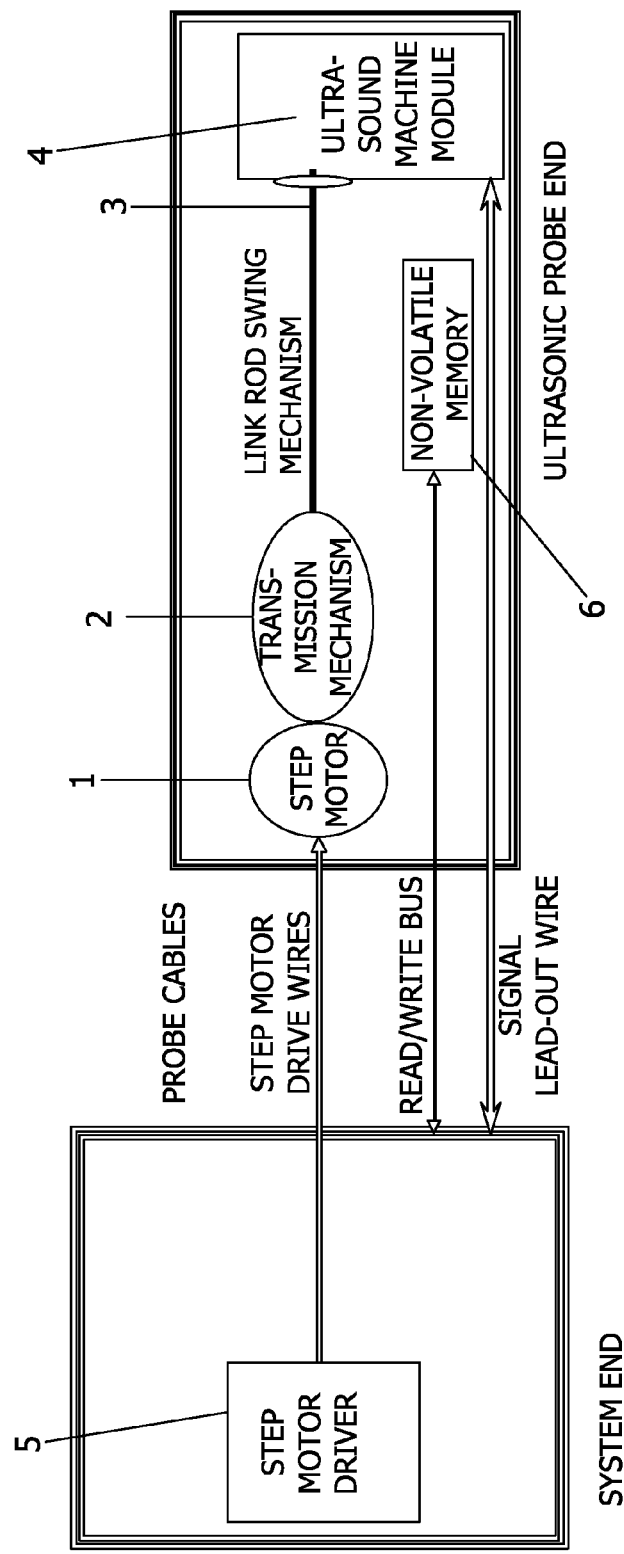
FIG. 1 is a simplified structural view according to the prior real-time volume ultrasonic probe.

As illustrated in FIG. 1, it is a mechanical structural view of a typical real-time volume ultrasonic probe. According to the figure, it can be seen that the ultrasonic probe consists of a system end and an ultrasonic probe end. The two are connected with each other through probe cables. The key part in the mechanical structure of the ultrasonic probe is a step motor 1 and a transmission mechanism 2. A step motor driver 5 drives the step motor 1 to move via step motor drive wires. Then, the transmission mechanism 2 is engaged with a gear (not shown) to realize slowed output. One end of a link rod swing mechanism 3 is connected to the transmission mechanism 2 and the other end is connected to an ultrasonic machine module 4. The step motor 1 takes actions to drive the transmission mechanism 2 and then the transmission mechanism 2 drives the ultrasonic machine module 4 to swing back and forth. At present, a nonvolatile memory 6 in the ultrasonic probe is mainly used to store the serial number, the date of production, the manufacture's code and the probe code of the probe, etc.

Figure 2:
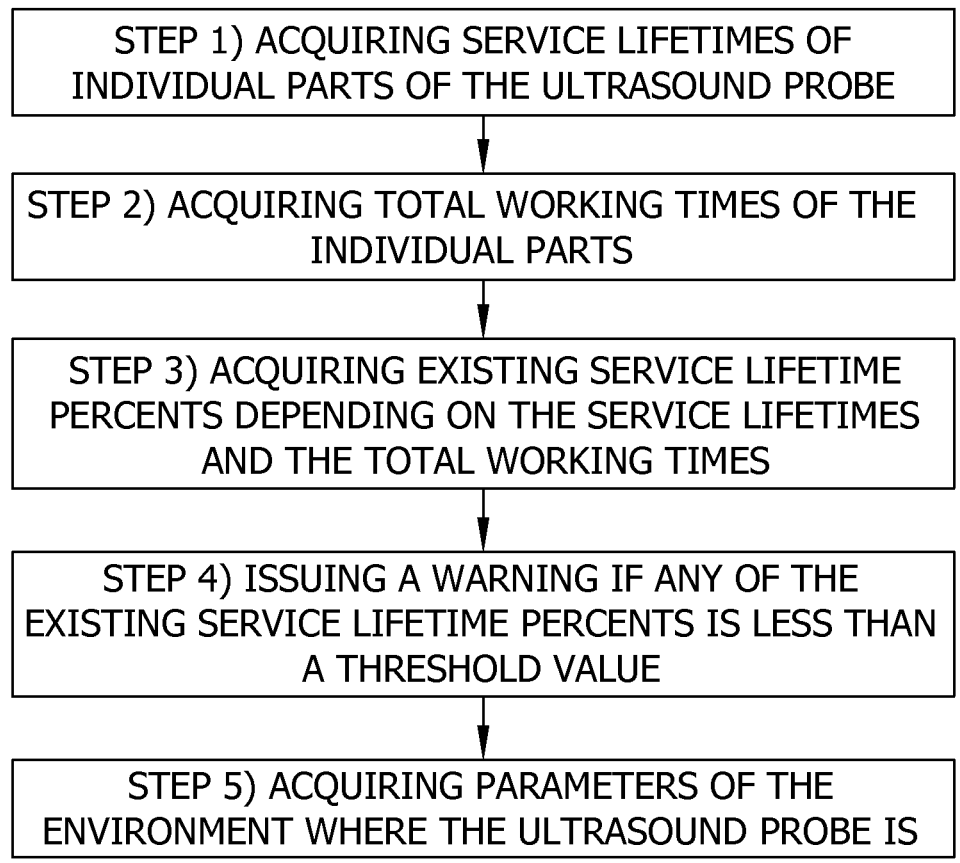
FIG. 2 is a flow chart of a real-time volume ultrasonic probe warning method according to the present invention.

As illustrated in FIG. 2, the early warning method for the ultrasonic probe according to the present invention includes:

step 1) acquiring service lifetimes of individual parts of the ultrasonic probe;

step 2) acquiring total working times of individual parts;

step 3) acquiring existing service lifetime percents depending on the service lifetimes and the total working times;

step 4) issuing a warning if any of the existing service lifetime percents is less than a threshold value.

According to the aforesaid contents, it can be seen that at first, the service lifetimes and total working times of individual parts of the ultrasonic probe are acquired, and then, the existing service lifetime percents are acquired depending on the service lifetimes and the total working times. If any of the existing service lifetime percent is less than a threshold value, the warning will be issued. The threshold value can be determined by a user. It is usually defined as 5% to 10%.

The warning can be sent to a maintenance station and so on by email. The warning can also be ejected in the form of a dialogue box and is displayed on a display interface. Certainly, those skilled in the art can use any mode of the warning as long as they can achieve it.

The service lifetimes of individual parts of the ultrasonic probe depend on the mechanical structure of the ultrasonic probe and the tape of the step motor. As for a particular ultrasonic probe, the service lifetimes are constant. They are always in the configuration file (resource file). When the ultrasonic probe is inserted into an ultrasonic system, the ultrasonic system will load this probe's setting and parameters from the configuration file. As for the different parts of the ultrasonic probe, the units of their service lifetimes are different. For example, the unit of the service lifetime of the step motor is hour. The unit of the service lifetime of the gearbox is cycle. The unit of the service lifetime of the belt system is centimeter, etc. Generally speaking, every type of ultrasonic probe has its own dedicated configuration file. Some general parameters of such a type of probe, such as probe code, average failure time, machine number, transmission ratio of each mechanical structure, step motor type, rated current of the step motor and so on, are recorded in the configuration file. The configuration file can be regarded as an identity document of the ultrasonic probe at the system end.

It is well-known that, every type of ultrasonic probe has the dedicated mechanical structure, namely, different gear ratios, different belt transfer coefficients and different diameters, etc. All of these are also called as characteristic parameters. These characteristic parameters and the particular application mode in which the ultrasonic probe is are used to work out the total working times. For a gearbox, calculation is done with the following equation:

a total working time of a gearbox=probe swing angle× link rod swing ratio×times of probe swing;

For a motor, calculation is done with the following equation:

a total working time of a motor=a working cycles of a gearbox×reduction ratio of a gearbox;

wherein, the reduction ratio of a gearbox and the link rod swing ratio are constants and stored in the configuration file. As for one type of probe, the two parameters are certain.

The probe swing angle and the times of probe swing are controlled by the system end of the ultrasonic probe and by a control instruction issued by the system itself.

For example, one 4D ultrasonic probe running at a certain application is designed as follows: 30 degree scan angle; volume rate is 4.2 Hz; the continuous working time is 3 minutes; the gear box ratio is 10, so the total working time of the gear box is:

4.2Hz×3 minutes×60(seconds/minute)×10×30degree/ 360degree=630cycles.

As for the other parts, except for the motor and the gear box, their total working times can be calculated depending on the parameters such as the transmission ratio of other parts to the transmission mechanism and so on. Herein, they are not discussed one by one in detail.

The acquired total working times can be stored in a nonvolatile memory 6 within the ultrasonic probe.

The existing service lifetime percents can be calculated by the following equation:

existing service lifetime percents=((service lifetimes− total working times)/service lifetimes)×100%.

Certainly, other modes known by those skilled in the art can also be used for calculation.

As illustrated in FIG. 2, the method for warning prior to the failure of the ultrasonic probe according to the present invention further comprises step 5): acquiring parameters of the environment where the ultrasonic probe is. The environment parameters can include the real-time voltage, the real-time electric current, temperature and so on. During application of the ultrasonic probe, acquisition of the parameters of the environment where it is can help the service person to find the root cause of the failure of the ultrasonic probe and can help the service person to remove faults and improve products to a large extent.

In addition, the environment parameters can also be stored in the nonvolatile memory 6 within the ultrasonic probe.

Although the aforesaid contents are described according to the sequence of step 1), step 2), step 3), step 4), and step 5), those skilled in the art can understand that the present invention is not only limited to the described sequence. It can be realized by any sequence or order. For example, the step 5 is firstly carried out, etc.

Figure 3:
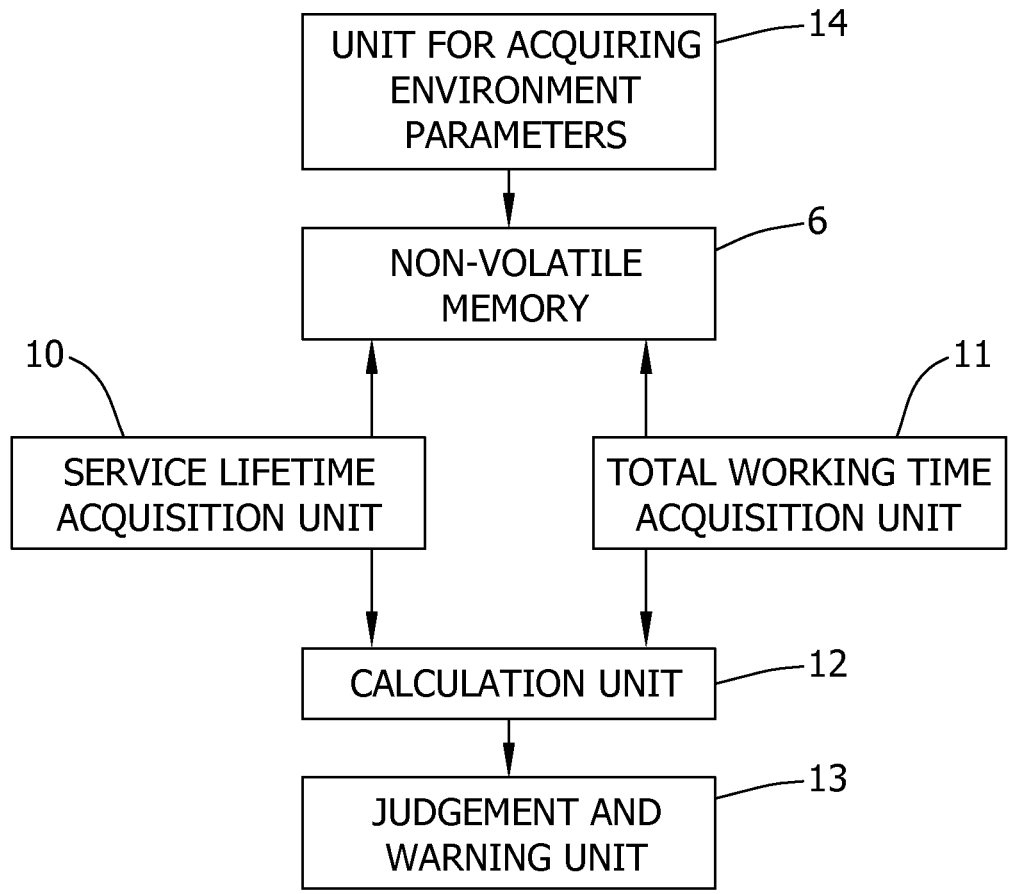
FIG. 3 is a structural view of a real-time volume ultrasonic probe warning device according to the present invention.

Correspondingly, the present invention also discloses an early warning ultrasonic device for the ultrasonic probe. As illustrated in FIG. 3, the early warning device includes a service lifetime acquisition unit 10 for acquiring service lifetimes of individual parts of the ultrasonic probe, a total working time acquisition unit 11 for acquiring total working times of individual parts of the ultrasonic probe, a calculation unit 12 for working out existing service lifetime percents depending on the service lifetimes and the total working times, and a judgment and warning unit 13 for judging if any of the existing service lifetime percents is less than a threshold value, and issuing a warning if the existing service lifetime is less than a threshold value.

Herein, the warning can be delivered to the user or an administrator by email. It can also be displayed on a display interface. Of course, those skilled in the art can use any mode that they have known to issue the warning. The service lifetimes can be stored in the configuration file. The service lifetimes acquisition unit 10, the total working time acquisition unit 11, calculation unit 12 and the judgment and warning unit 13 can be separate parts and can also be integrated with a major control unit (not shown) at the system end of the ultrasonic probe.

The total working time acquisition unit 11 also includes a total working time acquisition unit of a gearbox, configured to calculate the total working time of the gearbox using the following equation:

probe swing angle×link rod swing ratio×times of probe swing.

The total working time acquisition unit also includes a total working time acquisition unit of a motor, configured to calculate the total working time of the motor using the following equation: gearbox's working cycles×gearbox's reduction ratio.

The acquired total working times can be stored in the nonvolatile memory 6 within the ultrasonic probe.

The calculation unit 12 performs calculation by the following equation:

existing service lifetime percents=((service lifetimes−total working times)/service lifetimes)×100%.

Again, as illustrated in FIG. 3, the early warning device for the failure of the ultrasonic probe according to the present invention further comprises a unit for acquiring environment parameters 14 which is used for acquiring parameters of the environment where the ultrasonic probe is. The environment parameters are stored in the nonvolatile memory 6. The environment parameters can include a real-time voltage, a real-time electric current and temperature, etc. The environment parameters shall include the whole environment parameters of the ultrasonic parameters that those skilled in the art currently know and what they will know in the future.

Figure 4:
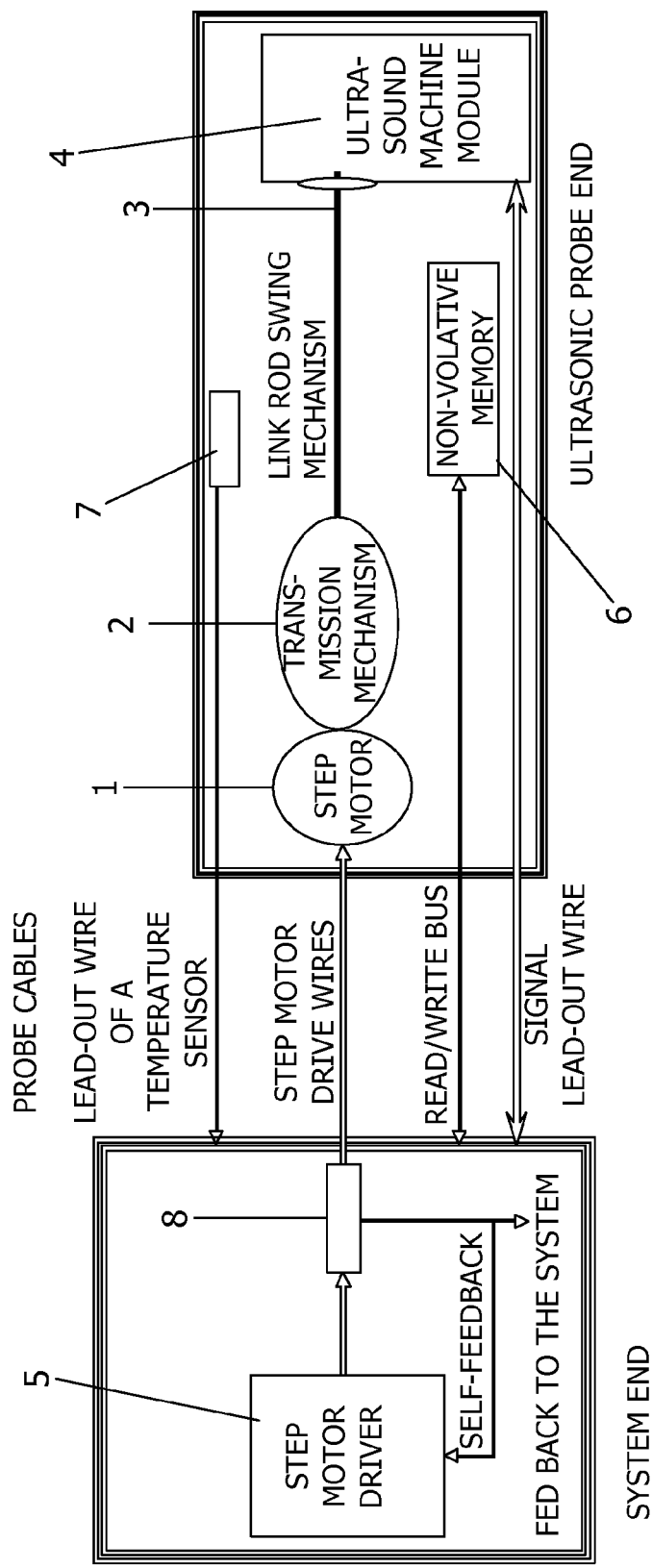
FIG. 4 is a simplified structural view of an improved real-time volume ultrasonic probe.

The unit for acquiring environment parameters 14, as illustrated in FIG. 4, includes a temperature sensor 7 disposed at the top of the ultrasonic probe and a current and voltage detector 8 disposed between a step motor driver 5 and a step motor 1. The temperature sensor 7 is used for sensing temperature. The current and voltage detector 8 is used for measuring the real-time voltage and the real-time current of the step motor 1. As for the temperature sensor 7 and the current and voltage detector 8, those skilled in the art can use any type of temperature sensor 7 and any type of current and voltage detector 8 as long as they know.

The current and voltage detector 8 and the temperature sensor 7 are used for detecting the voltage, the current and the internal environment temperature when the probe is working. The three values are stored in real time in the nonvolatile memory with the total working time.

On the other hand, the present invention further discloses an ultrasonic apparatus. It comprises the early warning device for the ultrasonic probe disclosed above.

The early warning method and device for an ultrasonic probe according to the present invention can be applied to any ultrasonic apparatus.

Although the particular embodiments of the present invention have been described in combination with the figures, various adjustments, modifications and equivalent replacements on the present invention can be done for those skilled in the art without departing from the spirit and scope of the present invention. These adjustments, modifications and equivalent replacements will fall within the spirit and scope of the attached claims.

What is claimed is:

1. An early warning method for use with an ultrasonic probe, said early warning method comprising:
    acquiring service lifetimes of individual parts of the ultrasonic probe;
    acquiring total working times of the individual parts;
    acquiring existing service lifetime percents depending on the service lifetimes and the total working times; and
    issuing a warning if any of the existing service lifetime percents is less than a threshold value, wherein acquiring total working times of the individual parts comprises:
        for a gearbox, calculating the total working time of the gearbox using the following equation:

a total working time of a gearbox=probe swing angle×link rod swing ratio×times of probe swing; and for a motor, calculating the total working time of the motor using the following equation:

a total working time of a motor=working cycles of a gearbox×reduction ratio of a gearbox.

2. The early warning method for an ultrasonic probe according to claim 1, wherein the service lifetimes are present in a configuration file.

3. The early warning method for an ultrasonic probe according to claim 1, further comprising storing the obtained total working times in a nonvolatile memory within the ultrasonic probe.

4. The early warning method for an ultrasonic probe according to claim 3, wherein acquiring existing service lifetime percents comprises calculating the existing service lifetime percents using the following equation:

existing service lifetime percents=((service lifetimes−total working times)/service lifetimes)×100%.

5. The early warning method for an ultrasonic probe according to claim 1, further comprising acquiring parameters of the environment where the ultrasonic probe is.

6. The early warning method for an ultrasonic probe according to claim 5, further comprising storing the environment parameters in a nonvolatile memory.

7. The early warning method for an ultrasonic probe according to claim 6, wherein the environment parameters include a real-time voltage, a real-time electric current and temperature.

8. The early warning method for an ultrasonic probe according to claim 7, wherein the warning is delivered to a maintenance station by email.

9. The early warning method for an ultrasonic probe according to claim 7, wherein the warning is presented in the form of a dialogue box and is displayed on a display interface.

10. An early warning device for use with an ultrasonic probe, said early warning device comprising:
 a service lifetime acquisition unit configured to acquire service lifetimes of individual parts of the ultrasonic probe;
 a total working time acquisition unit configured to acquire total working times of the individual parts of the ultrasonic probe, said total working time acquisition unit further configured to:
  calculate, for a gearbox, the total working time of the gearbox using the following equation:

probe swing angle×link rod swing ratio×times of probe swing; and calculate, for a motor, the total working time of the motor using the following equation:

working cycles of a gearbox×reduction ratio of a gearbox;

a calculation unit configured to calculate existing service lifetime percents depending on the service lifetimes and the total working times; and
 a judgment and warning unit configured to determine whether any of the existing service lifetime percents is less than a threshold value, and to issue a warning if the existing service lifetime is less than the threshold value.

11. The early warning device for an ultrasonic probe according to claim 10, wherein the service lifetimes are present in a configuration file.

12. The early warning device for an ultrasonic probe according to claim 10, further comprising a nonvolatile memory within the ultrasonic probe, said nonvolatile memory configured to store the obtained total working times of the individual parts.

13. The early warning device for an ultrasonic probe according to claim 12, wherein said calculation unit is configured to calculate the existing service lifetime percents using the following equation:

existing service lifetime percents=((service lifetimes−total working times)/service lifetimes)×100%.

14. The early warning device for an ultrasonic probe according to claim 10, further comprising a unit configured to acquire environment parameters configured to acquire parameters of an environment where the ultrasonic probe is operated.

15. The early warning device for an ultrasonic probe according to claim 14, wherein the environmental parameters are stored in a nonvolatile memory.

16. The early warning device for an ultrasonic probe according to claim 15, wherein the environment parameters include a real-time voltage, a real-time electric current and temperature.

17. The early warning device for an ultrasonic probe according to claim 16, wherein the warning is delivered to a maintenance station by email.

18. An ultrasonic apparatus comprising:
 an ultrasonic probe comprising a plurality of individual parts; and
 an early warning device comprising:
  a service lifetime acquisition unit configured to acquire service lifetimes of individual parts of the ultrasonic probe;
  a total working time acquisition unit configured to acquire total working times of the individual parts of the ultrasonic probe, said total working time acquisition unit further configured to:
   calculate, for a gearbox, the total working time of the gearbox using the following equation:

probe swing angle×link rod swing ratio×times of probe swing; and calculate, for a motor, the total working time of the motor using the following equation:

working cycles of a gearbox×reduction ratio of a gearbox;

a calculation unit configured to calculate existing service lifetime percents depending on the service lifetimes and the total working times; and
  a judgment and warning unit configured to determine whether any of the existing service lifetime percents is less than a threshold value, and to issue a warning if the existing service lifetime is less than the threshold value.

* * * * *